(12) United States Patent  
Leddy et al.

(10) Patent No.: US 9,506,085 B2  
(45) Date of Patent: Nov. 29, 2016

(54) AMMONIA PRODUCTION USING BIOELECTROCATALYTICAL DEVICES

(71) Applicant: UNIVERSITY OF IOWA RESEARCH FOUNDATION (UIRF), Iowa City, IA (US)

(72) Inventors: Johna Leddy, Iowa City, IA (US); Timothy Michael Paschkewitz, Morrisville, NC (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 13/931,368

(22) Filed: Jun. 28, 2013

(65) Prior Publication Data

US 2014/0011252 A1 Jan. 9, 2014

Related U.S. Application Data

(60) Provisional application No. 61/666,356, filed on Jun. 29, 2012.

(51) Int. Cl.
| | |
|---|---|
| *C12P 3/00* | (2006.01) |
| *C12M 1/00* | (2006.01) |
| *C12M 1/42* | (2006.01) |
| *C12N 11/14* | (2006.01) |
| *C12N 9/06* | (2006.01) |
| *C12N 13/00* | (2006.01) |
| *C12M 1/12* | (2006.01) |
| *C12N 9/02* | (2006.01) |

(52) U.S. Cl.
CPC ............... *C12P 3/00* (2013.01); *C12M 23/20* (2013.01); *C12M 25/08* (2013.01); *C12M 35/02* (2013.01); *C12N 9/0044* (2013.01); *C12N 9/0095* (2013.01); *C12N 9/0097* (2013.01); *C12N 11/14* (2013.01); *C12N 13/00* (2013.01); *Y02P 20/52* (2015.11)

(58) Field of Classification Search
CPC .......... H01M 8/00; H01M 8/14; H01M 8/16; C25B 1/00; C25B 11/00; C25B 11/04; C25B 11/12; C25B 11/14; C12N 1/00; C12N 1/12; C12P 1/00; C12P 13/00
See application file for complete search history.

(56) References Cited

U.S. PATENT DOCUMENTS

| | | | |
|---|---|---|---|
| 7,745,023 B2 | 6/2010 | Flickinger et al. | |
| 2004/0101741 A1 | 5/2004 | Minteer et al. | |
| 2005/0095466 A1 | 5/2005 | Minteer et al. | |
| 2005/0176131 A1* | 8/2005 | Flickinger et al. | 435/243 |
| 2009/0136827 A1 | 5/2009 | Minteer et al. | |
| 2011/0092726 A1 | 4/2011 | Clarke | |
| 2011/0256602 A1 | 10/2011 | Kistenmacher et al. | |
| 2013/0039833 A1 | 2/2013 | Zullo | |
| 2013/0052689 A1 | 2/2013 | Banta et al. | |

OTHER PUBLICATIONS

Spiller, H. et al. 1986. Isolation and characterization of nitrogenase-derepressed mutant strains of cyanobacterium Anabaena variabilis. Journal of Bacteriology 165(2): 412-419. specif. pp. 412, 414, 417.*

Tanaka, K. et al. 1988. Effects of light on the electrical output of bioelectrochemical fuel-cells containing Anabaena variabilis M-2: Mechanism of the post-illumination burst. Journal of Chemical Techology and Biotechnology 42:235-240. specif. pp. 235, 236.*

Su, W. et al. 2012. Dissimilatory nitrate reduction by Pseudomonas alcaliphila with an electrode as the sole elec tron donor. Biotechnology and Bioengineering 109: 2904-2910. specif. pp. 2905, 2907, 2909.*

Schrautemeier et al. 1985. A distinct ferredoxin for nitrogen fixation isolated from heterocysts of the cyanobacterium Anabaena variabilis. FEBS Letters 184(2): 304-308. specif. p. 304.*

PubChem. APCD. Datasheet [online]. NCBI, NIH. Create date: Mar. 27, 2005. [retrieved on Mar. 23, 2015]. Copyright NCBI.NLM. NIH. Bethesda, MD. Retrieved from the Internet: <URL: http://pubchem.ncbi.nlm.nih.gov/compound/517348#section=Top>. pg. 2.*

Ullman's Encyclopedia of Industrial Chemistry. Anion exchange resins.Ion Exchangers.Wiley-VCH Verlag GmbH (publisher). Copyright 2012. Wiley-VCH Verlag GmbH & Co. KGaA. Ed.: Francois de Dardel, Thomas V. Arden. Weinheim, Germany. p. 477.*

Herrero, A. et al. 1985. Regulation of nitrate reductase cellular levels in the cyanobacteria Anabaena variabilis and *Synechocystis* sp. FEMS Microbiology Letters 26: 21-25; specif. pp. 21, 25.*

Virdis, B. et al. 2008.Microbial fuel cells for simultaneous carbon and nitrogen removal. Water Research 42: 3013-3024. specif. pp. 3013, 3014, 3018.*

Torimura, M. et al. 2001. Electrochemical investigation of cyanobacteria *Synechococcus* sp. PCC7942-catalyzed photoreduction of exogenous quinones and photoelectrochemical oxidation of water. Journal of Electroanalytical Chemistry 496: 21-28. specif. pp. 21, 22.*

Kerby, N.W. et al. 1986. Photoproduction of ammonium by immobilized mutant strains of Anabaena variabilis. Applied Microbiology and Biotechnology 24: 42-46. specif. pp. 42, 43, 45.*

(Continued)

*Primary Examiner* — Renee Claytor  
*Assistant Examiner* — Sharon M Papciak  
(74) *Attorney, Agent, or Firm* — The Marbury Law Group, PLLC

(57) ABSTRACT

A device comprising at least one electrode and at least one cell such as *Anabaena variabilis* cyanobacteria disposed on said electrode for producing ammonia. A layer of polymer, such as ion exchange polymer, can be used to help immobilize the cells. Whole cells or partially disrupted cells can be used. A method and a system for producing ammonia, comprising contacting at least one cyanobacteria such as *Anabaena variabilis* cyanobacteria with a media with an electrochemical perturbation is disclosed. The potential enhances ammonia production.

30 Claims, 9 Drawing Sheets

(56) References Cited

OTHER PUBLICATIONS

Papageorgiou, G.C. et al. 1988. Entrapment of active ion-permeable cyanobacteria (Anacystis nidulans) in calcium alginate. Applied Microbiology & Biotechnology 29:565-571. specif. pp. 565, 566, 568.*

Martinez, et al., "Sustained Photoproduction of Ammonia From Nitrate or Nitrite by Permeabilized Cells of the Cyanobacterium Phormidium Laminosum", Journal of Photochemistry and Photobiology, B: Biology, vol. 3, pp. 269-279, (1989).

Musgrave, et al., "Sustained Ammonia Production by Immobilized Filaments of the Nitrogen-Fixing Cyanobacterium Anabaena 27893", Biotechnology Letters, vol. 4, No. 10, pp. 647-652, (1982).

Park, et al., "Photoproduction of Hydrogen, Hydrogen Peroxide and Ammonia Using Immobilized Cyanobacteria", Int. J. Hydrogen Energy, vol. 16, No. 5, pp. 313-318, (1991).

Brouers, et al., "Ammonia and Hydrogen Production by Immobilized Cyanobacteria", Journal of Biotechnology, vol. 3, pp. 307-321, (1986).

Kerby, et al., "Photoproduction of ammonium by immobilized mutant strains of Anabaena variabilis", Applied Microbiology Biotechnology, vol. 24, pp. 42-46, (1986).

Hameed, "Biotechnological Potential Uses of Immobilized Algae", Review, International Journal of Agriculture & Biology, 1560-8530, pp. 183-192, (Sep. 1, 2007).

Hallenbeck, "Immobilized microorganisms for hydrogen and ammonia production", Enzyme Microb. Technol., vol. 5, pp. 171-180, (May 1983).

Ramos, "Sustained Photoproduction of Ammonia from Dinitrogen and Water by the Nitrogen-Fixing Cyanobacterium *Anabaena* sp. Strain ATCC", Applied and Environmental Microbiology, vol. 48, No. 1, pp. 114-118, (Jul. 1984).

Paschkewitz, "Ammonia Production at Anabaena variabilis Modified Electrodes", Abstract #3591, Honolulu PRIME, The Electrochemical Society, University of Iowa, p. 1, (2012).

* cited by examiner

| [NO3-] | [NO2-] | [NADPH] | [Fd] | [NH3] uM | CODE | Description | pH |
|---|---|---|---|---|---|---|---|
| 100 uM | 0 | 0 | 0 | 7.33 | A1 | Effect of NO3- and [NH3] background | 7.32 |
| 300 uM | 0 | 0 | 0 | 4.74 | A2 | Effect of NO3- and [NH3] background | 8.85 |
| 500 uM | 0 | 0 | 0 | 8.57 | A3 | Effect of NO3- and [NH3] background | 7.15 |
| 0 | 100 uM | 0 | 0 | 5.82 | B1 | Effect of NO2- and [NH3] background | 6.7 |
| 0 | 300 uM | 0 | 0 | 5.91 | B2 | Effect of NO2- and [NH3] background | 7.01 |
| 0 | 500 uM | 0 | 0 | 15.66 | B3 | Effect of NO2- and [NH3] background | 7.18 |
| 500 uM | 500 uM | 0 | 0 | 13.82 | C | Effect of NO3- and NO2- | 8.59 |
| 500 uM | 100 uM | 0 | 0 | 9.31 | D | Effect of NO3- and NO2- | 7.86 |
| 100 uM | 500 uM | 0 | 0 | 6.11 | E | Effect of NO3- and NO2- | 7.88 |
| 0 | 0 | 0.01 mg/mL | 0 | 37.78 | F | Effect of NADPH and [NH3] background | 6.87 |
| 0 | 0 | 0 | 0.01 mg/mL | 3.59 | G | Effect of Fd and [NH3] background | 6.82 |
| 0 | 0 | 0.01 mg/mL | 0.01 mg/mL | 21.54 | H | Effect of NADPH and Fd | 6.51 |
| 500 uM | 0 | 0.01 mg/mL | 0.01 mg/mL | 21.63 | I | Effect of NO3- with NADPH and Fd | 6.92 |
| 0 | 500 uM | 0.01 mg/mL | 0.01 mg/mL | 19.08 | J | Effect of NO2- with NADPH and Fd | 6.67 |
| 500 uM | 500 uM | 0.01 mg/mL | 0.01 mg/mL | 13.66 | K | Effect of NO3- and NO2- with NADPH and Fd | 6.43 |
| 500 uM | 0 | 0.01 mg/mL | 0 | 26.34 | L | Effect of NO3- and NADPH (NR enzyme) | 6.7 |
| 0 | 500 uM | 0 | 0.01 mg/mL | 29.86 | M | Effect of NO2- and Fd (NiR enzyme) | 6.33 |

FIGURE 9

AMMONIA PRODUCTION USING BIOELECTROCATALYTICAL DEVICES

RELATED APPLICATIONS

This Application claims priority to U.S. provisional application 61/666,356 filed Jun. 29, 2012, which is hereby incorporated herein by reference in its entirety for all purposes.

BACKGROUND

Ammonia is a highly demanded commodity with multiple uses. Most of the ammonia produced today is for use as fertilizer. However, ammonia also shows promise for use in power generation. It can be used as a fuel in internal combustion engines and ammonia fuel cells and as a hydrogen source for hydrogen fuel cells.

Ammonia is commercially produced using the Haber Bosch process. However, this process is energetically and environmentally taxing, consuming 1% of energy worldwide. The Haber Bosch process requires high temperatures (350°-700° C.) and pressures (150-500 atm). Furthermore, the $H_2$ used in this process is obtained from steam reformation of $CH_4$ that releases CO as a byproduct. Energy consumption of a typical Haber Bosch production facility is 28 GJ/ton $NH_3$ produced and originates from resource limited fuels such as coal. Finally, this process is, at best, <20% efficient.

There exists a need for alternative financially and energetically cost-effective means for generating ammonia.

SUMMARY

Embodiments described herein include compositions, devices, and systems, and methods of making and using same.

One embodiment provides a device comprising at least one electrode and ammonia-producing cells disposed on the electrode. In one embodiment, the ammonia-producing cells are a cyanobacteria. In one embodiment, the ammonia-producing cells are a filamentous heterocystic cyanobacteria. In one embodiment, the ammonia-producing cells are genetically mutated. In one embodiment, the ammonia-producing cells are *Anabaena variabilis*. In one embodiment, the ammonia-producing cells are *Anabaena variabilis* which have a depressed nitrogenase level. In one embodiment, the ammonia-producing cells are *Anabaena variabilis* strain SA-1. In one embodiment, the ammonia-producing cells are at least partially disrupted. In one embodiment, the ammonia-producing cells comprise at least nitrogenase enzyme and/or nitrate/nitrite reductase enzyme. In one embodiment, the electrode is a carbon electrode, a metal electrode, or a semiconductor electrode. In one embodiment, the electrode is coated at least in part with a polymer. In one embodiment, the electrode is a carbon electrode. In one embodiment, the electrode is a glassy carbon electrode.

In one embodiment, the device further comprises at least one layer disposed on the electrode adapted to immobilize the cell on the electrode. In one embodiment, the layer is a polymer layer. In one embodiment, the layer comprises at least one ion exchange polymer. In one embodiment, the layer comprises at least one ion exchange polymer, wherein the ion exchange polymer comprises an ion exchange polymer comprising a fluorocarbon backbone. In one embodiment, the layer comprises at least one ion exchange polymer, wherein the ion exchange polymer comprises an ion exchange polymer comprising a fluorocarbon backbone and sulfonic acid groups which are modified to reduce acidity. In one embodiment, the layer is about 1 micron to about 100 microns thick. In one embodiment, the electrode is a carbon electrode or a metal electrode and the cells are cyanobacteria, and optionally wherein the layer comprises at least one ion exchange polymer.

Another embodiment provides a method comprising: providing at least one device comprising at least one electrode and ammonia-producing cells disposed on the electrode, providing the cells with an appropriate nitrogen-containing enzyme substrate, and producing ammonia from the cells. In one embodiment, the electrode is subjected to an electrical potential in the production of ammonia. In one embodiment, the electrode is subjected to a constant potential or a cycled voltametry. In one embodiment, the production of ammonia is carried out with use of an electrolyte solution. In one embodiment, the production of ammonia is carried out with use of a media which comprises at least one of nitrate, nitrite, and reduced nicotinamide adenine dinucleotide phosphate (NADPH). In one embodiment, the media further comprises ferredoxin. In one embodiment, the ammonia-producing cells are *Anabaena variabilis*.

Another embodiment provides a system comprising the device of claim 1 as at least one working electrode, and also comprising at least one counter electrode, and further comprising at least one electrolyte solution, and optionally further comprising at least one reference electrode. In one embodiment, the system further comprises additional components in the electrolyte solution to enhance ammonia production. In one embodiment, the system further comprises at least one fixed potential source or at least one potentiostat to polarize the electrodes. In one embodiment, the system components are adapted for cyclic voltammetry.

In another embodiment, a device is provided comprising at least one electrode and ammonia-producing enzyme disposed on the electrode. In one embodiment, the ammonia-producing enzyme comprise at least nitrogenase enzyme and/or nitrate/nitrite reductase enzyme. In one embodiment, the electrode is a carbon electrode, a metal electrode, or a semiconductor electrode. In one embodiment, the electrode is coated at least partially with a polymer. In one embodiment, the electrode is a carbon electrode. In one embodiment, the electrode is a glassy carbon electrode.

In one embodiment, the device further comprises at least one layer disposed on the electrode adapted to immobilize the enzyme on the electrode. In one embodiment, the layer is a polymer layer. In one embodiment, the layer comprises at least one ion exchange polymer. In one embodiment, the layer comprises at least one ion exchange polymer, wherein the ion exchange polymer comprises a fluorocarbon backbone. In one embodiment, the layer comprises at least one ion exchange polymer, wherein the ion exchange polymer comprises a fluorocarbon backbone and sulfonic acid groups which are modified to reduce acidity. In one embodiment, the layer is about 1 micron to about 100 microns thick. In one embodiment, the electrode is a carbon electrode or a metal electrode, and wherein the layer comprises at least one ion exchange polymer.

At least one advantage for at least one embodiment is that ammonia production can be achieved at ambient temperature and pressure. The process is significantly less energy intensive and less environmentally taxing than the Haber-Bosch process. Unlike Haber-Bosch processes, this device and process can be established locally and is not constrained to a commercial processing plant. Distributed, on-site production of ammonia reduces transportation costs.

At least one additional advantage for at least one embodiment is that a biological organism is used that naturally produces ammonia. With electrochemistry, ammonia production can be increased compared to production without the electrochemistry.

At least one additional advantage for at least one embodiment is that the overall process is environmentally friendly as, for example, waste products can be used to fuel the process. For example, wastes of nitrate and nitrite are generated by fertilizer decomposition and farm animals. Runoff from nitrate and nitrite is considered an environmental and health hazard. Use of these oxidation products to generate ammonia contributes to environmental mediation.

BRIEF DESCRIPTION OF THE DRAWINGS

FIG. 9. Experimental conditions. Study of the effects of $NO_3^-$, $NO_2^-$, ferredoxin (Fd), and NADPH additives to 0.1 M Na$_2$SO$_4$. In each case, cyclic voltammetric experiments were performed and [$NH_3$] was measured after they were completed. pH of the final solutions were also measured at the completion of the CVs.

DETAILED DESCRIPTION

Introduction

All references described herein are hereby incorporated by reference in their entireties, including the thesis, Timothy M. Paschkewitz, Ph.D Thesis, University of Iowa (2012) ("Ammonia Production at Ambient Temperature and Pressure: An Electrochemical and Biological Approach").

No admission is made that any cited reference is prior art.

Use of biological cells for commercial production of chemicals or chemical reactions is known in the art. See, for example, US Patent Publication Nos. 2011/0092726, 2011/0256602, 2013/0039833, and 2013/0052689 and U.S. Pat. No. 7,745,023

Ammonia-Producing Cells

Ammonia-producing cells and bacteria are known in the art, including immobilized forms of the cells. See, for example, "Ammonia and Hydrogen Production by Immobilized Cyanobacteria," Brouers et al., *J. Biotechnology*, 3 (1986) 307-321; "Photoproduction of . . . Ammonia Using Immobilized Cyanobacteria," Park et al., *Int. J. Hydrogen Energy*, Vol. 16, No. 5, pp. 313-318, 1991; "Sustained Ammonia Production by Immobilized Filaments of the Nitrogen-Fixing Cyanobacterium Anabaena ATCC 27893," Musgrave et al., *Biotechnology Letters*, Vol. 4, No. 10, 647-652 (1982); Martinez et al., *J. Photochemistry and Photobiology*, B: Biology, 3 (1989) 269-279; Kerby et al., Appl. Microbiol. Biotechnol (1986) 24: 42-46; Hallenbeck, Enzyme Microb. Technol., 1983, Vol. 5, May, 171; and Ramos, *Applied and Environmental Microbiology*, July 1984, p. 114-118.

For purposes herein, a cell can be a single cell or a plurality or group of cells, including a cell culture.

Many blue green algae produce ammonia. See, Hameed, *International J. of Agriculture & Biology*, 1560-8530/2007/09-1-183-192.

Figure 2:
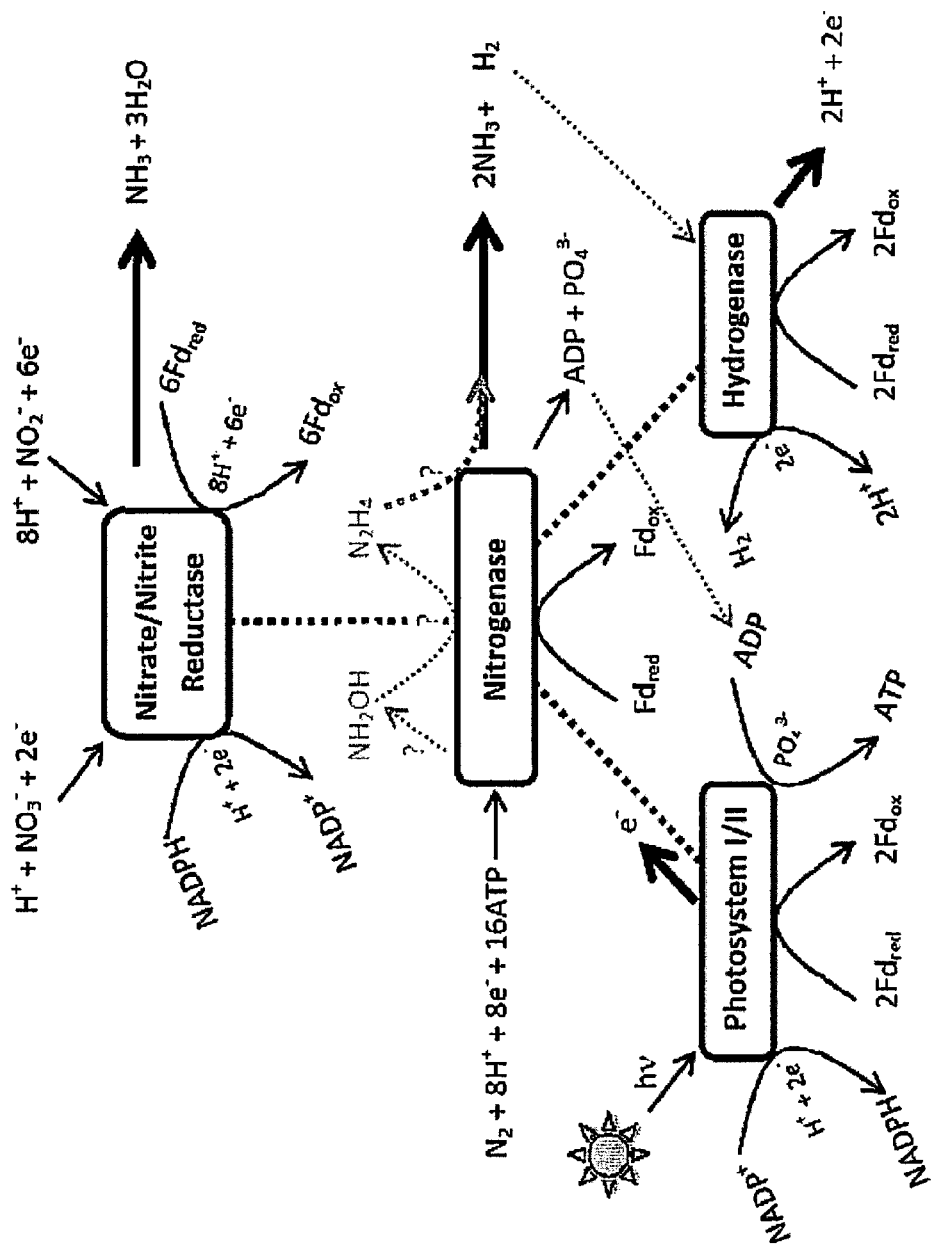
FIG. 2 illustrates what are believed to be interrelated reaction centers in Anabaena variabilis and similarly other cyanobacteria. Nitrogenase was known in the prior art for its ability to generate $NH_3$ from $N_2$. Peripheral reaction centers showing shared mediators, co-factors, reactants, and products. Major reaction centers are shown in boxes and are Photosystem I/II, Hydrogenase, Nitrogenase, and Nitrate/Nitrite Reductase.

Herein, photosynthetic cyanobacteria Anabaena variabilis can produce ammonia when driven by voltammetric perturbation. Within *Anabaena variabilis* are at least two enzyme pathways for ammonia production: nitrogenase and nitrate/nitrite reductase. Nitrogenase can fix atmospheric nitrogen $N_2$ to form ammonia. Nitrate/nitrite reductase can reduce nitrate and then nitrite to form ammonia. When grown in a low nitrate environment, the algae can produce ammonia through the nitrogenase pathway. When cells are grown on nitrate rich media, the cells can lose nitrogenase after several generations; these cells can use nitrate/nitrite reductase to produce ammonia. As shown in FIG. 2, the nitrogenase cycle can be coupled to photosystem I and II and nitrate/nitrite reductase and thereby dependent on ferredoxin, $NADP^+$, and very heavily dependent on ATP. On the other hand, nitrate/nitrite reductase is dependent on $NADP^+$ and ferredoxin but not ATP.

Figure 3:
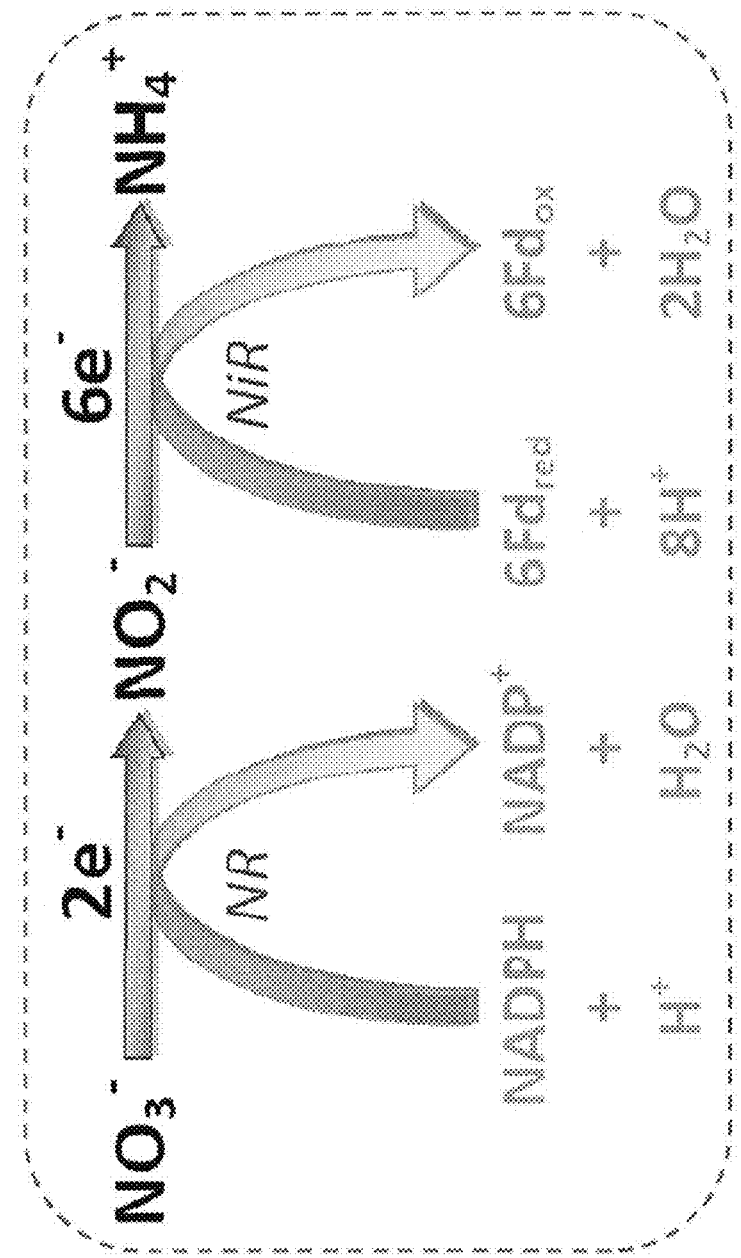
FIG. 3 shows a schematic representation of the nitrate/nitrite reductase enzyme. The nitrite reductase enzyme is used by cyanobacteria to produce $NH_3$. In parallel with nitrogenase that produces ammonia from dinitrogen, the reductase enzymes ensure adequate ammonia be available to the cell. Ammonia production is especially favored by nitrite reductase in environments with sufficient nitrate and nitrite. The scheme shown highlights the dependence upon NAD(P)H and ferredoxin.

Physiologically, the nitrate/nitrite reductase enzyme (NRE) is largely responsible for producing $NH_3$ when there is sufficient nitrate/nitrite available that is not necessary for nitrogenase to produce ammonia from. Nitrate and nitrite are substrates for the NRE found in *Anabaena variabilis* and other cyanobacteria and algae. As shown in FIG. 3, the electrochemical reactions in NRE for producing ammonia are:

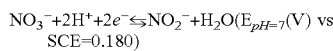
$$NO_3^- + 2H^+ + 2e^- \leftrightarrows NO_2^- + H_2O \, (E_{pH=7}(V) \text{ vs SCE} = 0.180)$$

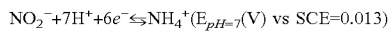
$$NO_2^- + 7H^+ + 6e^- \leftrightarrows NH_4^+ \, (E_{pH=7}(V) \text{ vs SCE} = 0.013)$$

Figure 1:
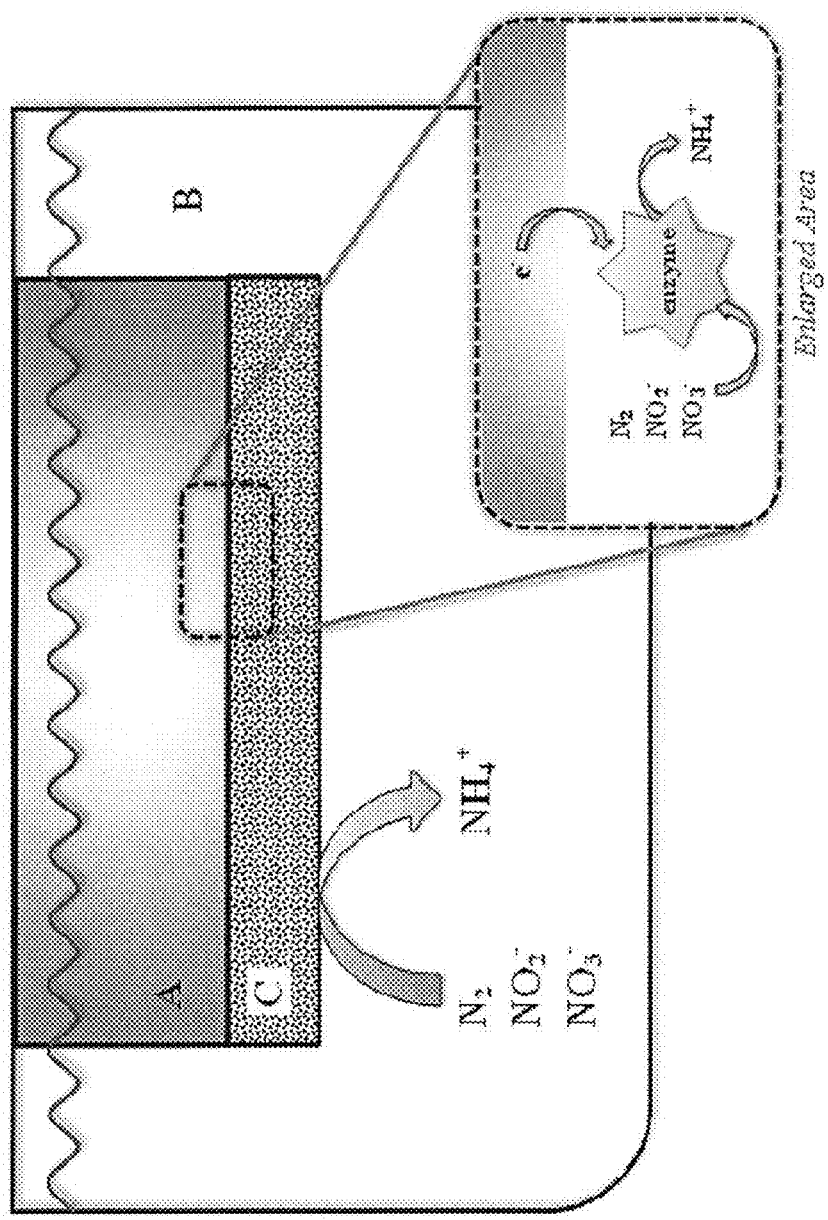
FIG. 1 shows a schematic of an example of a bioelectrocatalytic device for ammonia production. In this embodiment, at a glassy carbon electrode (A), ammonia producing cyanobacteria are immobilized in a modified cation exchange polymer (Nafion®) film (C). The test solution (B) contains enzyme substrates. Interaction of these substrates with enzymes ($N_2$ for nitrogenase; $NO_2^-$ and $NO_3^-$ for nitrate-nitrite reductase) under voltammetric perturbation supplies electrons as shown in the enlarged image) to release $NH_4^+$ into the external media.).

Many embodiments disclosed here relate to a device for producing ammonia, comprising at least one electrode and at least one ammonia-producing cell, such as for example a cyanobacteria such as *Anabaena variabilis* cyanobacteria, immobilized on said electrode for producing ammonia, as shown in FIG. 1. Other strains of cyanobacteria exist which could be manipulated in the manner described herein. Other examples of cells and bacteria which can be used include mutated or genetically modified *Anabaena variabilis* and other strains of *Anabaena variabilis* and other algae.

Cells can be adapted by man for use in the embodiments described herein. Genetic engineering can be used if appropriate. The *Anabaena variabilis* can be, for example, a wild-type strain of *Anabaena variabilis* strain, such as commercial strain ATCC #29413. The *Anabaena variabilis* can be, for example, a strain with a depressed level of nitrogenase, such as *Anabaena variabilis* strain SA-1. The amount of nitrogenase in the *Anabaena variabilis* used in the device can be, for example, less than 80%, or less than 50%, or less than 30%, or less than 20%, or less than 10% of the amount of nitrogenase in *Anabaena variabilis* strain ATCC #29413.

Whole cells or partially disrupted cells can be used. In one embodiment, whole cells are used. However, in another embodiment, the cells can be at least partially disrupted before use for ammonia production. The disruption can be done by known chemical or physical methods. For example, sonication or enzymatic breakdown using lysozyme can be be used. Cell disruption can help eliminate membrane effects. Enhanced current responses can be achieved.

Cells Disposed on or Immobilized on Electrode

The disposition and/or immobilization of cells on a substrate is known in the art including use of one or more immobilization layers. The cells, such as the *Anabaena variabilis* cyanobacteria, can be immobilized on the electrode by means known in the art. In some embodiments, the *Anabaena variabilis* cyanobacteria is immobilized on the electrode by at least one polymer, which can be, for example, a synthetic polymer such as, for example, an ion exchange polymer. The ion-exchange polymer can be, for example, a fluorinated sulfonic acid copolymer, such as a Nafion polymer, or derivative thereof. The ion-exchange copolymer can be, for example, a Nafion polymer modified with an ammonium cation such as, for example, an alkyl ammonium cation. The ion-exchange polymer can be, for example, a Nafion copolymer modified with trimethyloctadecylammonium bromide (TMODA). Such immobilized copolymers are described in, for example, US Patent Publications 2004/0101741; 2005/0095466; and 2009/0136827 (Minteer et al.) which are incorporated herein by reference in their entireties. In one embodiment, a mixture of the ion exchange polymer and the *Anabaena variabilis* cyanobacteria is immobilized onto the electrode in the form of a film.

Other immobilization methods for the cell on the electrode include, for example, use of another ion exchange polymer that can include but are not limited to poly(styrene sulfonate) and poly(styrene carbonate) and their derivatives. An electron conductive polymer can be used; these include, for example, polyaniline and polythiophenes such as, for example, PEDOT. Inert polymers that form sufficiently porous layer to allow flow of solution and substrates but viscous enough to maintain the cells at the electrode surface are possible. This is not limited to but include polyvinyl alcohol and Ficoll®.

In some cases, one can attach a cell to an electrode without the polymer layer. Gravity could be used, for example, to hold the cells against the electrode surface. In addition, cells can be grown onto or into the electrode surface. In one embodiment, cells can be grown in a shallow pond where an electrode such as carbon paper or carbon cloth floats just below the air-water interface. Polarization of the electrode may be used to enhance adhesion and interactions of the cells with the electrode.

Electrode

Electrodes for driving an electrochemical perturbation are known in the art. The electrode can be, for example, a carbon-based or metal-based electrode or a semiconductor electrode. With a semiconductor electrode, the photovoltaic could be built right into the cell. The electrode can be, for example, a glassy carbon electrode or a high-surface-area carbon electrode such as a carbon mesh electrode. The electrode can be porous or non-porous. Other examples of electrodes include but are not limited to carbon paper, carbon cloth, vitrious carbon, carbon nanotube modified current collectors, and boron doped diamond.

The electrode can be, for example, polarized to increase the production of ammonia by the *Anabaena variabilis* cyanobacteria. The electrode can, for example, have applied to it an electrical potential to create a potential gradient.

The shape and size of the electrode can be adapted for the scale of and type of reaction for ammonia production. Large area electrodes can be used for scale up. For example, a large sheet electrode floated near the air water interface of a waste confinement pond or natural pond or other body of water high in nitrate/nitrite would produce larger quantities of ammonia than a smaller cell designed to produce ammonia fuel for a fuel cell that powers a portable device.

The electrode can be, for example, at least partially coated by or shrouded by a polymer layer such as a fluorinate polymer for further protection. Some of the electrode, however, is exposed so as to have ammonia-generating cells disposed thereon.

Electrolyte Media

The device can comprise, for example, an electrolyte media contacting said cells, e.g., *Anabaena variabilis* cyanobacteria, wherein the media comprises nitrate. The amount of nitrate in the media can be, for example, at least 10 µM, or at least 20 µM, or at least 50 µM, or at least 100 µM, or at least 200 µM, or at least 500 µM.

The device can comprise, for example, an electrolyte media contacting said cells, e.g., *Anabaena variabilis* cyanobacteria, wherein the media comprises nitrite. The amount of nitrite in the media can be, for example, at least 10 µM, or at least 20 µM, or at least 50 µM, or at least 100 µM, or at least 200 µM, or at least 500 µM.

The device can comprise, for example, an electrolyte media contacting said cells, e.g., *Anabaena variabilis* cyanobacteria, wherein the media comprises a mixture of nitrate and nitrite. The total amount of nitrate and nitrite in the media can be, for example, at least 10 µM, or at least 20 µM, or at least 50 µM, or at least 100 µM, or at least 200 µM, or at least 500 µM.

The media can comprise, for example, nicotinamide adenine dinucleotide phosphate ($NADP^+$) or its reduced form (NADPH). The amount of NADPH in the media can be, for example, at least 0.0001 mg/mL, or at least 0.001 mg/mL, or at least 0.002 mg/mL, or at least 0.005 mg/mL, or at least 0.01 mg/mL.

The media can comprise, for example, ferredoxin. The amount of ferredoxin in the media can be, for example, at least 0.0001 mg/mL, or at least 0.001 mg/mL, or at least 0.002 mg/mL, or at least 0.005 mg/mL, or at least 0.01 mg/mL.

The media can further comprise, for example, an inhibitor of ammonium reuptake, such as methionine-D,L-sulfoximine (MSX). This provides an advantage and enhance amounts of ammonia production.

The media can be, for example, BG-11 or $BG-11_0$, or a modified BG-11 or a modified $BG-11_0$.

Systems and Devices

The systems and devices described herein can comprise other components, including electrodes such as a counter electrode and/or a reference electrode, as known to those skilled in the art of fabricating electrochemical systems and cyclic voltametry. Optionally, the device can further comprise a power source such as, for example, contact to the power grid or a battery or a wind turbine or a photovoltaic cell coupled to the electrode to provide electrical potential.

Method for Producing Ammonia

Many embodiments disclosed here relate to a method for producing ammonia, comprising contacting at least one device as described herein (e.g., at least one electrode including the cell such as *Anabaena variabilis* cell) with at least one nitrogen source (such as dinitrogen, nitrate, or nitrite) in the presence of, or with application of, an electrochemical perturbation. For purposes herein, ammonia production is also equivalent to ammonium production.

The electrochemical perturbation can be applied across, for example, an electrode coupled with a second electrode so that a potential is established. The electrodes are thereby polarized. The electrical potential difference applied by the electrodes can be, for example, about 0.001 V to 10 V or about 0.005 V to about 4 V, or about 0.02 V to about 2 V or about 0.05 V to about 1.2 V, or about 0.1 V to about 1.0 V, or about 0.2 V to about 0.8 V, or about 0.3 V to about 0.6 V.

The electrode can comprise, for example, a cell such as a bacteria cell such as cyanobacteria cells (e.g., *Anabaena variabilis* cyanobacteria) immobilized thereon. Alternatively, the cells, e.g., *Anabaena variabilis* cyanobacteria, can be present in an electrolyte media to which the electrode applies an electrical potential. The cells can contact the electrode for at least short periods of time. The cell could be disposed on the electrode by, for example, electrostatics, physiosorption, or chemisorption.

The *Anabaena variabilis* can be, for example, a wild-type strain of *Anabaena variabilis* strain, such as commercial strain ATCC #29413. The *Anabaena variabilis* can be, for example, a strain with a depressed level of nitrogenase, such as *Anabaena variabilis* strain SA-1. The level of nitrate and nitrate reductase is increased in the presence of sufficient nitrate/nitrite.

The *Anabaena variabilis* cyanobacteria can be immobilized on the electrode by means known in the art. In some embodiments, the *Anabaena variabilis* cyanobacteria is immobilized on the electrode by at least one ion exchange polymer. The ion-exchange polymer can be, for example, a Nafion polymer or derivative thereof. The ion-exchange polymer can be, for example, a Nafion polymer modified with an alkyl ammonium cation. The ion-exchange polymer can be, for example, a Nafion polymer modified with trimethyloctadecylammonium bromide (TMODA). In one embodiments, a mixture of the ion exchange polymer and the *Anabaena variabilis* cyanobacteria is immobilized onto the electrode in the form of a film.

The electrolyte media can comprise, for example, nitrate as a nitrogen source. The electrolyte media can comprise, for example, nitrite as a nitrogen source. The electrolyte media can comprise, for example, nicotinamide adenine dinucleotide phosphate ($NADP^+$) or its reduced form (NADPH). The electrolyte media can comprise, for example, ferredoxin. The electrolyte media can further comprise, for example, an inhibitor of ammonium reuptake, such as methionine-D,L-sulfoximine (MSX).

The method described herein can achieve an ammonium production quantity that is, for example, at least 10%, or at least 20%, at least 50%, at least 100%, at least 200%, at least 500%, or at least 1000% higher in quantity than the ammonium production of the corresponding method in which the *Anabaena variabilis* is not electrochemically perturbed. The amount can be converted to a rate if a fixed time reference is used.

Ammonia can be produced with or without light.

Optionally, the method can further comprising providing electrical potential from a photovoltaic cell coupled to the electrode.

Ammonia is produced by nitrate and nitrite reductase and/or nitrogenase by a cyanobacteria embedded in a TMODA-Nafion film on a surface, whether the surface is a polarized electrode or not.

Method for Making Device

Additional embodiments relate to a method for making the aforementioned device (ammonia-producing device), which can comprise contacting, for example, *Anabaena variabilis* cyanobacteria with an electrode. The cells, e.g., *Anabaena variabilis* cyanobacteria, can be deposited on a surface of the electrode. The cells, e.g., *Anabaena variabilis* cyanobacteria can be immobilized on the electrode by at least one ion exchange polymer. In one embodiment, the method comprises (a) providing a mixture of an ion exchange polymer and *Anabaena variabilis* cyanobacteria, (b) immobilizing the mixture onto an electrode as a film, and optionally (c) contacting the electrode with an electrolyte media, wherein the electrolyte comprises at least one of nitrate, nitrite, and NADPH.

The thickness of the film comprising the *Anabaena variabilis* and the ion exchange polymer can be, for example, about 0.1-200 micron, or about 0.5-100 micron, 1 micron to 100 microns, or about, 1-50 micron, or about 2-20 micron.

Use of Enzymes Without Cells

Another embodiment is a device comprising at least one electrode and ammonia-producing enzyme disposed on the electrode. The ammonia-producing enzyme can comprise, for example, at least nitrogenase enzyme and/or nitrate/nitrite reductase enzyme. Enzyme immobilization methods are known in the art including use of modified Nafion films. If an inhibitor for the enzyme exists, such as oxygen, then the exclusion of the inhibitor needs to be partially or totally carried out.

Applications

The devices and methods described herein are suitable for producing ammonia as an inexpensive, environmentally friendly, alternative to the Haber Bosch method. In particular, the devices and methods described herein can be used to produce ammonia on a farmland, where the ammonia produced can either be directly used as fertilizer or converted and stored in anhydrous form for fuel purposes.

In another example, the device to produce ammonia also remediates nitrate and nitrite wastes associated with animal confinement facilities and in places where runoff of fertilizer from a prior year accumulates. In particular, a smaller ammonia generating device can be used to make fuel for a fuel cell used in portable electronics. A closed loop hybrid system could include algae generation of ammonia from nitrate/nitrite that is oxidized in a fuel cell to nitrate/nitrate that is in turn returned to ammonia by the ammonia producing device. Such a closed loop system where at least one electrode is common to the ammonia generation and the ammonia consumption processes. A system can be made where the ammonia producing device is applied to a semiconductor electrode that generates the electricity/potential to polarize the ammonia producing device. A device can be mounted to a roof that converts nitrate and nitrite into ammonia that powers a fuel cell to provide power to a house, business, mobile device, or vehicle. Another device exploits the 0.6 mM concentration of nitrate in human urine to generate ammonia as a fuel or fertilizer. Such a fuel system might be of use in an off grid situation or in portable applications such as for camping equipment.

Additional embodiments are provided in the following non-limiting working examples.

WORKING EXAMPLES

Example 1

Cell Culture

Two strains of *Anabaena variabilis* were used. The wild type cell *Anabaena variabilis* was purchased from the American Type Culture Collection (ATCC #29413) and subsequently subcultured in the laboratory. A mutant of this wild type was created by K. T. Shanmugam of the University of Florida in the 1980's. This strain of ATCC #29413 is nitrogenase depressed and called *Anabaena variabilis* SA-1 This means that the ammonia produced by the cells is not taken up by normal enzyme pathways such as the glutamine synthetase pathway and are instead excreted into the external environment. Both the wild type ATCC #29413 and *Anabaena variabilis* SA-1 were cultured in the exact same manner.

BG-$11_0$ was selected as the culture medium. It is a metal-salt broth prepared in the lab. It contained no source of fixed (reduced) nitrogen species, thus eliciting a genetic response within the cells to generate heterocysts and thus, the nitrogenase enzyme.

1-L bottles of BG-$11_0$ are prepared as follows:
1. Autoclave 1-L media bottle prior to use.
2. Obtain the 20-mL vial of "Common Chemicals". Add 10-mL of DI water and shake bottle to dissolve.
3. Add this "Common Chemicals" mixture to the 1-L media bottle. Rinse the 20-mL vial out several times with DI water and add it to the media bottle.
4. Add enough DI water to bring the volume to 1-L.
5. With a calibrated pH electrode, adjust the pH of the solution to 7.1 using HCl and NaOH as necessary.
6. Autoclave the solutions at 121° C. for 15 minutes.
7. Once cooled, add 1-mL of the "Trace Metals" mix solution to each bottle. Shake Well. Store in refrigerator.

The final concentrations of chemicals used for media preparation are as follows:

| "Common Chemical" | Final Concentration (M) |
|---|---|
| NaCl | $4.28 \times 10^{-4}$ |
| $K_2HPO_4$ | $2.30 \times 10^{-4}$ |
| $MgSO_4 \cdot 7H_2O$ | $3.04 \times 10^{-4}$ |
| $CaCl_2 \cdot 2H_2O$ | $2.45 \times 10^{-4}$ |
| Citric Acid | $3.12 \times 10^{-5}$ |
| Ferric Ammonium Citrate | $2.14 \times 10^{-5}$ |
| EDTA | $2.69 \times 10^{-6}$ |
| $Na_2CO_3$ | $1.89 \times 10^{-4}$ |

| "Tract Metal" | Final Concentration (M) |
|---|---|
| $H_3BO_3$ | $4.63 \times 10^{-5}$ |
| $MnCl_2 \cdot 4H_2O$ | $5.96 \times 10^{-6}$ |
| $ZnSO_4 \cdot 7H_2O$ | $7.72 \times 10^{-7}$ |
| $Na_2MoO_4 \cdot 2H_2O$ | $1.61 \times 10^{-6}$ |
| $CuSO_4 \cdot 5H_2O$ | $3.16 \times 10^{-7}$ |
| $Co(NO_3)_2 \cdot 6H_2O$ | $1.26 \times x10^{-7}$ |

The cells were continuously cultured at 32° C. μE/mol·s light delivered by two full spectrum fluorescent bulbs within the incubator. Cells were cultured in 250-mL baffled flasks containing 125-mL of media-cell suspensions. These were constantly agitated through use of an orbital shaker set to rotate at 125 RPM.

Example 2

Device Fabrication

TMODA-Nafion is prepared with 1100EW 5% (m/m) Nafion suspension in alcohols (Ion Power) and solid trimethyloctadecylammonium bromide (Aldrich). A 20% molar excess of solid TMODA is dissolved into an ethanolic suspension (as shown by the calculation below, 0.0184 g TMODA/mL Nafion suspension is used). This suspension is added to a weighing dish and allowed to dry in a desiccator for 24 hours. Following drying, water is added to the dish for 24 hours to leech out remaining Br ions. Following subsequent washing with deionized water, the solid that remains is added to a 70% ethanol/water. It is agitated with commercial vortexing and sonication until all solid is suspended in the ethanol/water solution.

$$\left(\frac{5 \text{ g Nafion}}{100 \text{ g Solution}}\right)\left(\frac{0.86 \text{ g solution}}{\text{mL solution}}\right)\left(\frac{\text{mol Nafion}}{1100 \text{ g Nafion}}\right)$$

$$\left(\frac{1.2 \text{ mol } TMODA}{\text{mol Nafion}}\right)\left(\frac{392.52 \text{ g } TMODA}{\text{mol } TMODA}\right) = \frac{0.0184 \text{ g } TMODA}{\text{mL Nafion}}$$

TMODA-Nafion is well-mixed by vortexing samples in 15-mL conical flask for 5 minutes. 5-mL of *Anabaena variabilis* cell suspensions are obtained and vortexed for 1 minute to break up any large clusters that formed in the culture media. Depending on the density of cells desired, the resultant cell suspension can be diluted with BG-11$_0$ media.

25 µl of cell suspension of desired density is mixed together with 25 µl of TMODA-Nafion suspension and vortexed for 1 minute. This is the immobilized cell polymer suspension.

9 µl of the immobilized cell polymer suspension is applied to the surface of a 5 mm OD glassy carbon working electrode. After 5 minutes, the cells are mixed on the surface to result in a less heterogeneous film. The film is allowed to dry fully (about 10 minutes) during with all solvent (ethanol/water) evaporates leaving behind a 10 µm-thick film of TMODA-Nafion containing *Anabaena variabilis* filaments.

Figure 4:
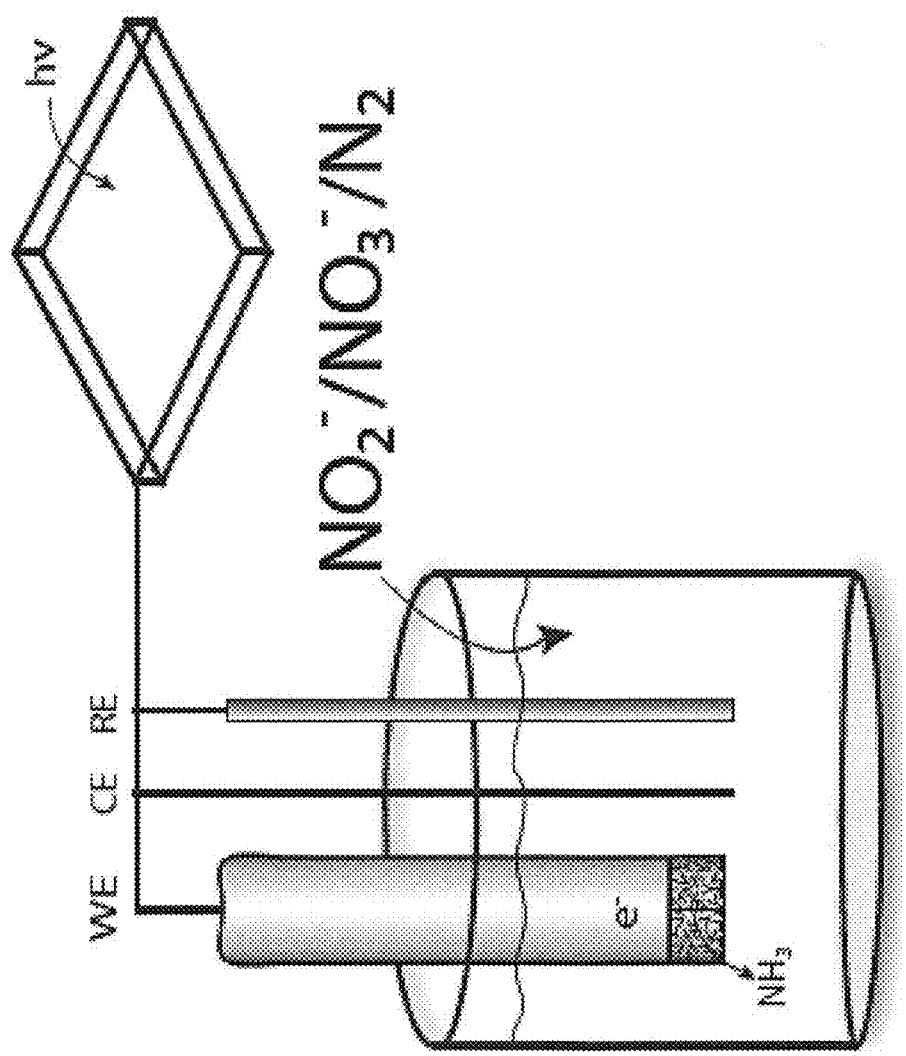
FIG. 4 shows one exemplary a bioelectrocatalytic device. Cells are immobilized to a working electrode (WE) with modified-Nafion. The electrode is polarized by a potential drop between the WE and counter electrode (CE). Measured potentials are compared to the internal redox potential of the reference electrode (RE). A nitrogen source is introduced into the device and is catalyzed to $NH_3$ by enzymes within the cells. Electric power is applied between the working electrode and counter electrode which electrocatalyzes the ammonia production. The power necessary to drive the reactions can optionally be supplied by an external photovoltaic source that harnesses light energy. A photovoltaic device is shown in the Figure.

The CV used a three electrode system that includes a saturated calomel reference electrode (SCE) and a glassy carbon working electrode modified with either whole cells or heterocysts supported in TMODA Nafion. The third electrode is a high surface area counter electrode. See FIG. 4. In cyclic voltammetry, the potential at the working electrode, here GC|TMODA Nafion+cells, was swept linearly from a potential where no faradaic (electron transfer at the electrode) current flowed to a potential where the direction of the potential sweep was reversed; the sweep was continued, often cycled back to the initial potential. In some cases, the potential cycled between the initial and switching potential multiple times.

NH$_3$ production from this bioelectrocatalytic device was followed with an ammonia ion-selective electrode. Dissolved NH$_3$ was gaseous and passed through the hydrophobic membrane of the ammonia ion selective electrode (ISE). The pH change of the electrolyte solution on the other side of the membrane caused by the diffused gas was sensed by the inner body of the ammonia electrode which is a pH electrode. The pH change was relative to the amount of dissolved NH$_3$ present and was measured with a pH or ion meter capable of voltage readings.

Example 3

Results

The main electroanalytical focus was to determine what was present at cell-modified electrodes that are observed as electroactive species in the cyclic voltammograms. Many chemical and environmental variables such as nitrogen containing species, air gases, possible mediating chemical species, pH, and light were examined. The electrochemical activity had demonstrated dependence upon chemical constituents and environmental variables including species generated by the partially reduced N$_2$, nitrogen containing species, and the addition of chemicals normally present in vivo. The major findings leading to initial modeling and energy-balance calculations are:

By subjecting the cell immobilized electrode to voltammetric perturbation, significantly more ammonia was produced than expected. In particular, low basal levels of ammonia production by batch (125-mL) cultures of *A. var.* were measured with an ammonia ion-selective electrode. This measurement represented the in vivo output of NH$_3$. This basal output of ammonia from 15-mL samples of well mixed cultures (where cells and debris are removed) was 1.6+/−0.4 µM. Following voltammetric perturbation of the same density of cells immobilized to the electrodes at various scan rates, average ammonia production for select experimental conditions increased to 15.4+/−5.1 µM.

The data are more consistent with the nitrate/nitrite reductase pathway for producing ammonia in *Anabaena variabilis* than the nitrogenase pathway. Further, it was observed that high fixed nitrogen in growth media resulted in more efficient NH$_3$ production.

Figure 5:
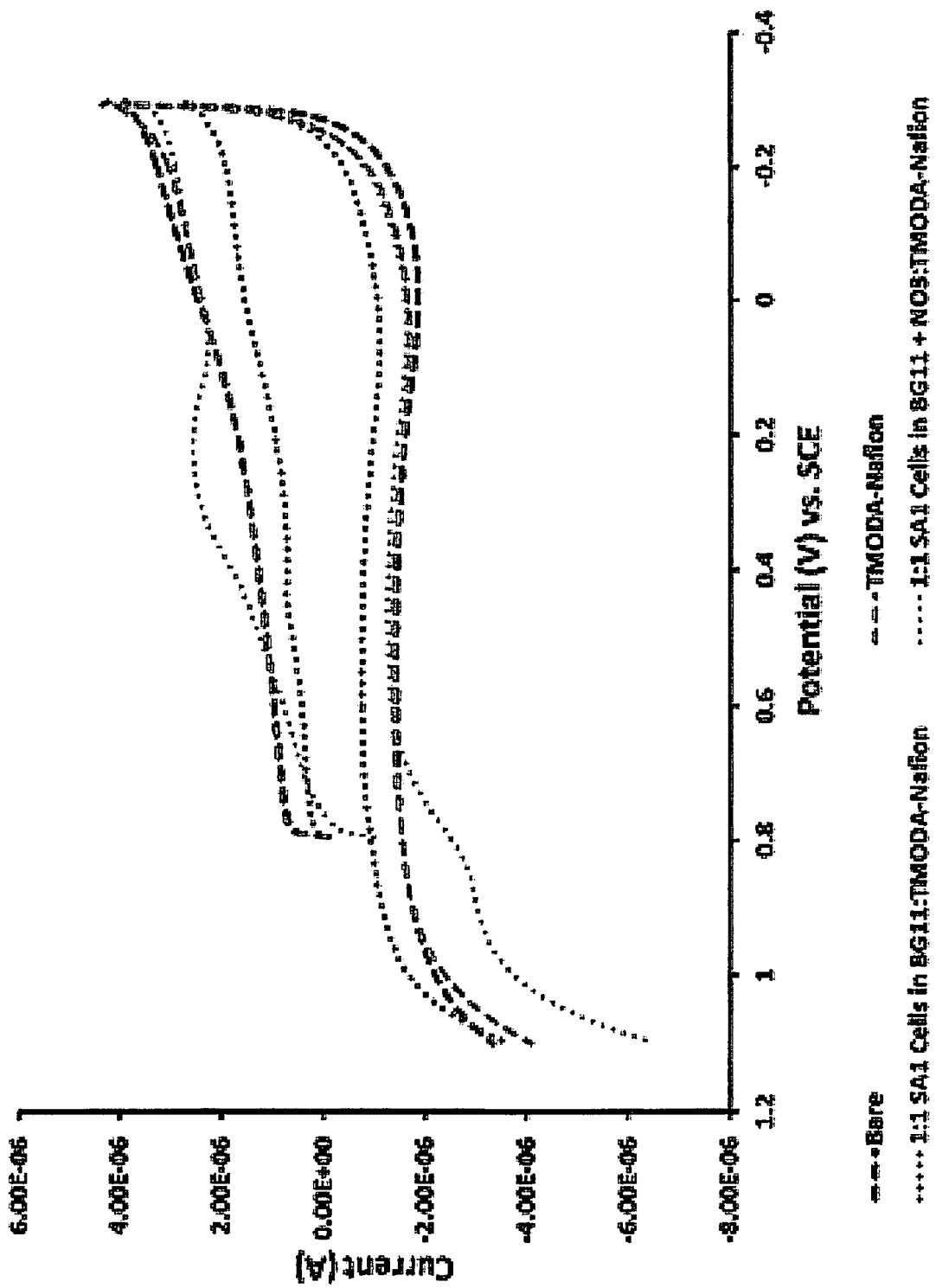
FIG. 5. Cyclic Voltammetric comparison of an unmodified glassy carbon electrode (dashed black), and glassy carbon electrode modified with 10 μm TMODA (dashed, gray), 1:1 Cells:TMODA-Nafion (dotted red, Nitrate-starved cells cultured in BG-11$_0$), and 1:1 Cells:TMODA-Nafion (dotted pink, nitrate-supplemented cells cultured in BG-11$_0$ with 17 mM NaNO$_3$). Background electrolyte is 0.1 M Na$_2$SO$_4$, Pt-mesh counter electrode (CE), SCE reference electrode, and scan rate of up to 75 mV/s. TMODA is trimethyl octadecyl ammonium that is exchanged into Nafion to produce the modified Nafion. The growth medium for the algae is BG-11$_0$.
Figure 6:
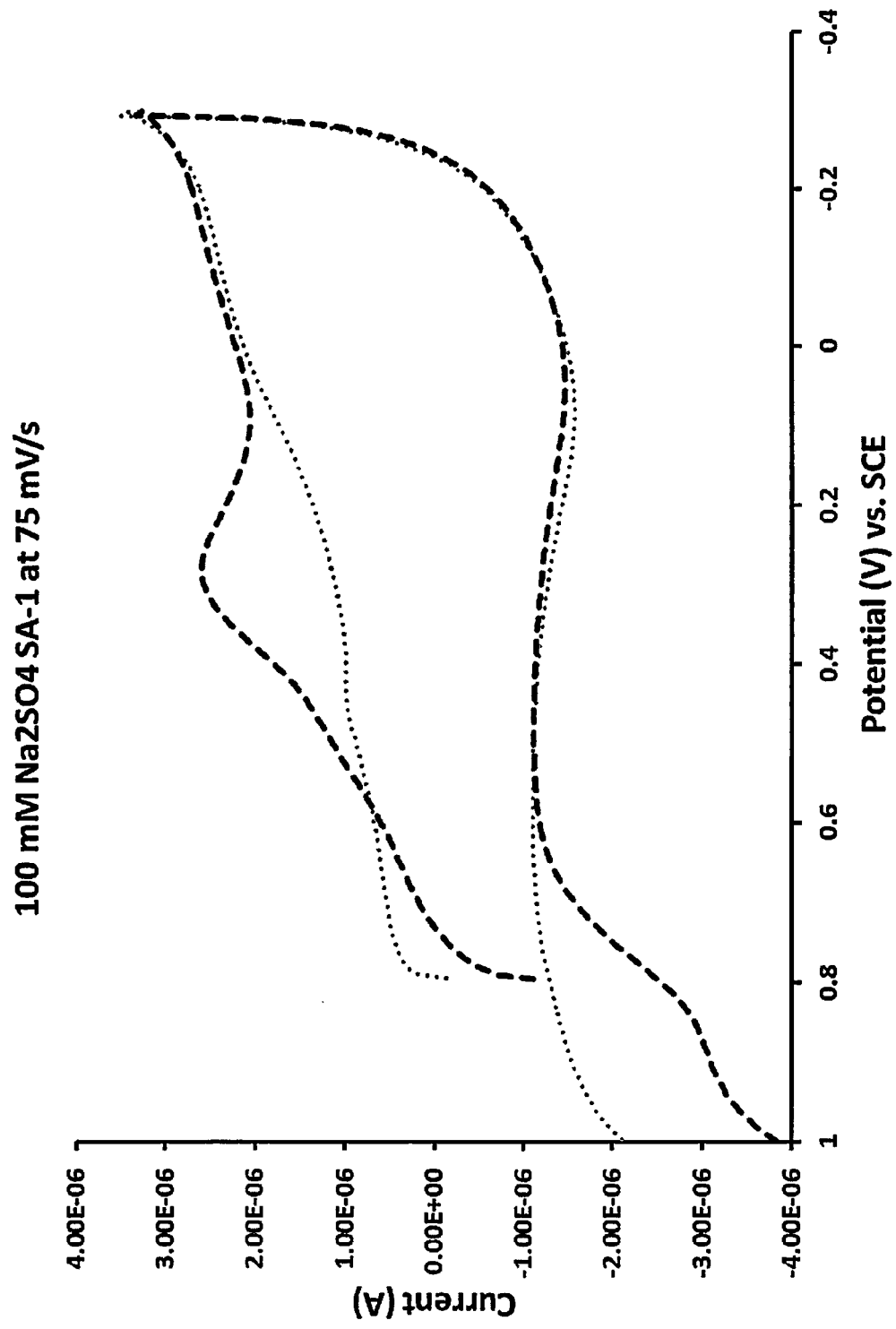
FIG. 6. Cyclic Voltammetric comparison of 1:1 Cells: TMODA-Nafion modified Glassy Carbon electrode (dotted pink, Nitrate-supplemented cells cultured in BG-11$_0$ with 17 mM NaNO$_3$), and 1:1 Cells:TMODA-Nafion modified Glassy Carbon electrode (dashed red, Nitrate-starved cells cultured in BG-11$_0$). Background electrolyte is 0.1 M Na$_2$SO$_4$, Pt-mesh counter electrode, SCE reference electrode, 75 mV/s.

Upon cyclic voltammetric analysis, cultures grown on NO$_3^-$ exhibited larger currents than from cells grown without nitrate/nitrite so dependent upon nitrogenase-produced NH$_3$, as shown in FIG. 5. If nitrogenase, or species directly involved with the action of the enzyme, were directly correlated to the analytical response from voltammetric perturbation, then under nitrate-supplemented conditions where there are few-to-no active nitrogenase-containing heterocysts present, no voltammetric waves should be present. As shown in FIG. 5, the opposite results were observed where the nitrate-supplemented cells exhibited higher current and more characteristic voltammetric responses than in the case normally observed where cells are starved of nitrate. These data indicated that nitrogenase is not the specific enzyme probed during voltammetric perturbation. There may be a correlation between electrochemical data and the nitrate/nitrite reductase enzyme. FIG. 6 compares a scale-adjusted overlay of both cells types, nitrogenase dependent and NRE dependent cultures.

Figure 7:
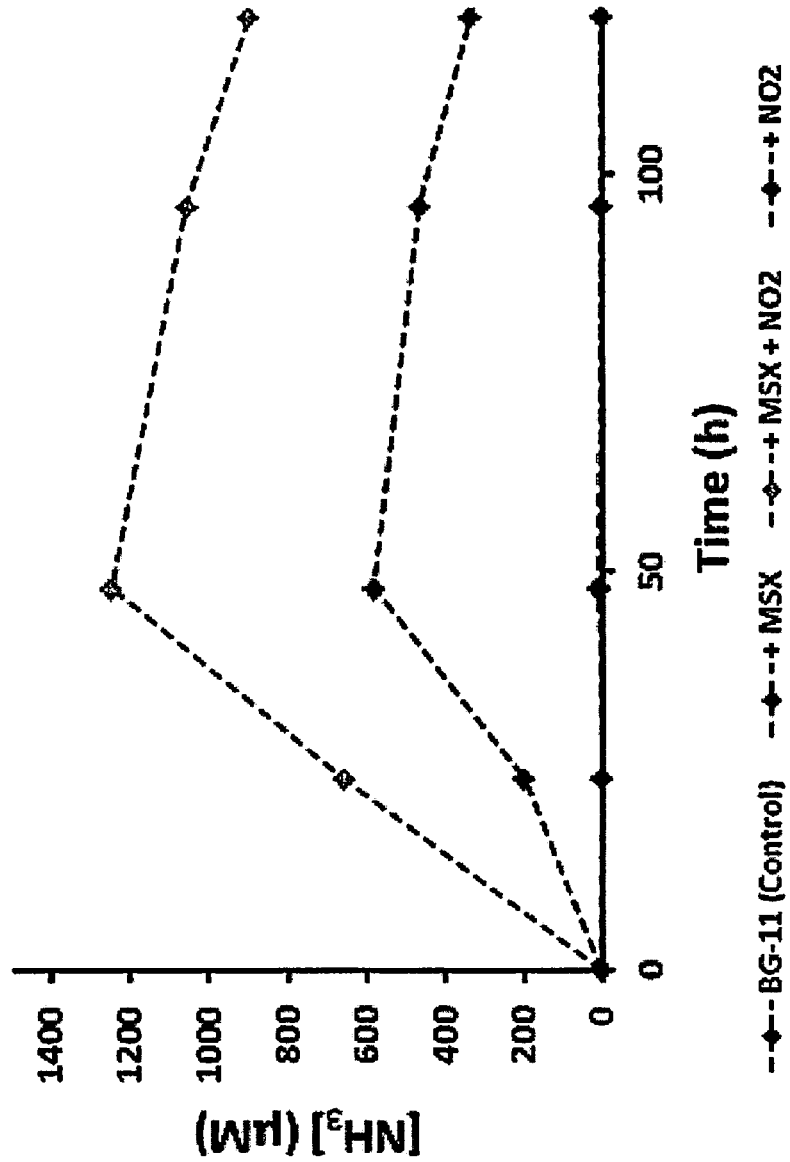
FIG. 7. $NH_3$ output from A. var. during media supplementation over a 4-day period. Control (BG-11$_0$ media, N-free, blue), MSX (inhibits reuptake of $NH_3$, red), MSX+ $NO_2^-$ (green), and $NO_2^-$ (purple). MSX=methionine D,L-sulfoximine, an amino acid analog which blocks the reuptake of $NH_4^+$.

Early work directed at increasing the output of NH$_3$ from the cells studied the effect of NO$_2^-$ supplementation. As shown in FIG. 7, in conjunction with methionine-D,L-sulfoximine (MSX), an amino acid analogue that blocks the reuptake of NH$_3$ by the glutamine synthetase pathway, NO$_2^-$ supplementation resulted in significantly higher measured NH$_3$ output from the cells as measured by an ammonia ion-selective electrode. These data suggested that when cells have a source of nitrite, the ferredoxin-dependent NRE may use it as a substrate for additional NH$_3$ production.

Figure 8:
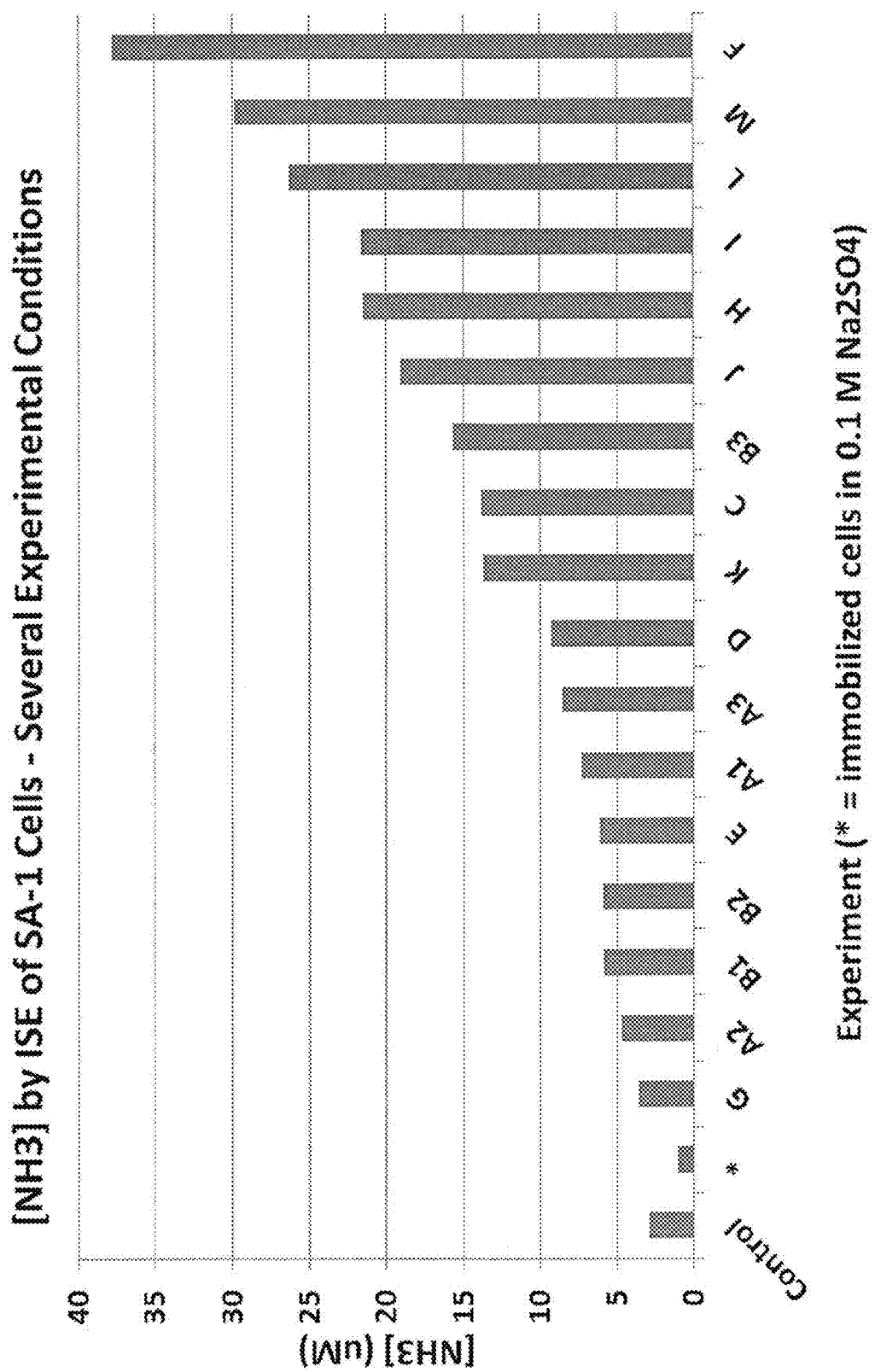
FIG. 8. [$NH_3$] as measured from spent 0.1 M Na$_2$SO$_4$ electrolyte. * is the experiment where cells were immobilized in 0.1 M Na$_2$SO$_4$ alone (no added source of N), while the control is a measure of [$NH_3$] from the media in which the cells are cultured. All other labels correspond to FIG. 9.

FIG. 8 shows representative NH$_3$ output from TMODA-Nafion immobilized *Anabaena variabilis* cells following cyclic voltammetric perturbation. The experimental conditions corresponding to the lettered bars are provided in FIG. 9. These data demonstrated that it is suitable to produce ammonia by contacting *Anabaena variabilis* cells with an electrolyte comprising at least one of nitrate, nitrite, and NADPH, in the presence of electrochemical perturbation provided by a polarized electrode.

In sum, while not limited by theory, ammonia likely was generated largely through the nitrate/nitrite reductase enzyme. Cells grown on nitrate rich media had no nitrogenase and produced more ammonia, as measured with a gas sensing ion selective electrode. Polarization of the electrode increased ammonia production almost ten-fold over unpolarized films. Electrodes modified with *Anabaena variabilis* in TMODA-Nafion but not polarized produced only baseline levels of ammonia, 2.8±0.4 µM after 10 minutes. Analogous electrodes that were polarized produced 22±8 µM after 10 minutes. Thus, electrode polarization coupled into the ammonia generating enzyme processes and increased ammonia production. At the electrode, enzymatic ammonia production increased because of the electrode generated reductive environment and likely production of mediators. As ammonia production increased, the reductive peak current increased.

Additional working examples and details are provided in the aforementioned PhD thesis of Timothy M. Paschkewitz which is incorporated herein by reference for its working examples.

What is claimed is:

1. An electrochemical system for use in the production of ammonia from cyanobacteria with the use of a polarized working electrode comprising:
at least one working electrode and ammonia-producing cells disposed on the working electrode, wherein the ammonia-producing cells are cyanobacteria,
at least one counter electrode, and
at least one electrolyte solution, and
wherein the system further comprises at least one fixed potential source or at least one potentiostat to polarize the electrodes, and
wherein the system provides for an ammonia production quantity that is at least 100% higher than the ammonia production quantity in which the working electrode is not polarized.

2. The system of claim 1, wherein the ammonia-producing cells are a filamentous heterocystic cyanobacteria.

3. The system of claim 1, wherein the ammonia-producing cells are genetically mutated.

4. The system of claim 1, wherein the ammonia-producing cells are *Anabaena variabilis*.

5. The system of claim 1, wherein the ammonia-producing cells are *Anabaena variabilis* strain SA-1.

6. The system of claim 1, wherein the ammonia-producing cells comprise at least nitrogenase enzyme and/or nitrate/nitrite reductase enzyme.

7. The system of claim 1, wherein the working electrode is a carbon electrode, a metal electrode, or a semiconductor electrode.

8. The system of claim 1, wherein the working electrode is coated at least in part with a polymer.

9. The system of claim 1, wherein the working electrode is a carbon electrode.

10. The system of claim 1, wherein the working electrode is a glassy carbon electrode.

11. The system of claim 1, wherein the system further comprises at least one layer disposed on the working electrode adapted to immobilize the cell on the electrode.

12. The system of claim 11, wherein the layer is a polymer layer.

13. The system according to claim 11, wherein the layer comprises at least one ion exchange polymer.

14. The system of claim 11, wherein the layer comprises at least one ion exchange polymer modified with alkyl ammonium cation.

15. The system of claim 11, wherein the layer comprises at least one ion exchange polymer, wherein the ion exchange polymer comprises an ion exchange polymer comprising a fluorocarbon backbone and sulfonic acid groups which are modified to reduce acidity.

16. The system of claim 11, wherein the layer is about 0.1 micron to about 200 microns thick.

17. The system of claim 11, wherein the working electrode is a carbon electrode or a metal electrode, and wherein the layer comprises at least one ion exchange polymer.

18. The system of claim 1, wherein the system further comprises additional components in the electrolyte solution to enhance ammonia production.

19. The system of claim 1, wherein the system components are adapted for cyclic voltammetry.

20. The system of claim 1, wherein the ammonia-producing cells are at least partially disrupted.

21. The system of claim 11, wherein the layer comprises at least one fluorinated ion exchange polymer.

22. The system according to claim 1, wherein the ammonia-producing cells disposed on the working electrode are attached to the electrode without a polymer layer.

23. The system according to claim 1, wherein the system provides for an ammonia production quantity that is at least 200% higher than the ammonia production quantity in which the working electrode is not polarized.

24. A method comprising: providing at least one system according to claim 1, providing the cells with an appropriate nitrogen-containing enzyme substrate, and producing ammonia from the cells.

25. The method of claim 24, wherein the working electrode is subjected to an electrical potential in the production of ammonia.

26. The method of claim 24, wherein the working electrode is subjected to a constant potential or a cycled voltammetry.

27. The method of claim 24, wherein the production of ammonia is carried out with use of a media which comprises at least one of nitrate, nitrite, and reduced nicotinamide adenine dinucleotide phosphate (NADPH).

28. The method of claim 27, wherein the media further comprises ferredoxin.

29. The method of claim 24, wherein the ammonia-producing cells are *Anabaena variabilis*.

30. The method of claim 24, wherein the production of ammonia is carried out with use of light.

* * * * *